Figure 1:
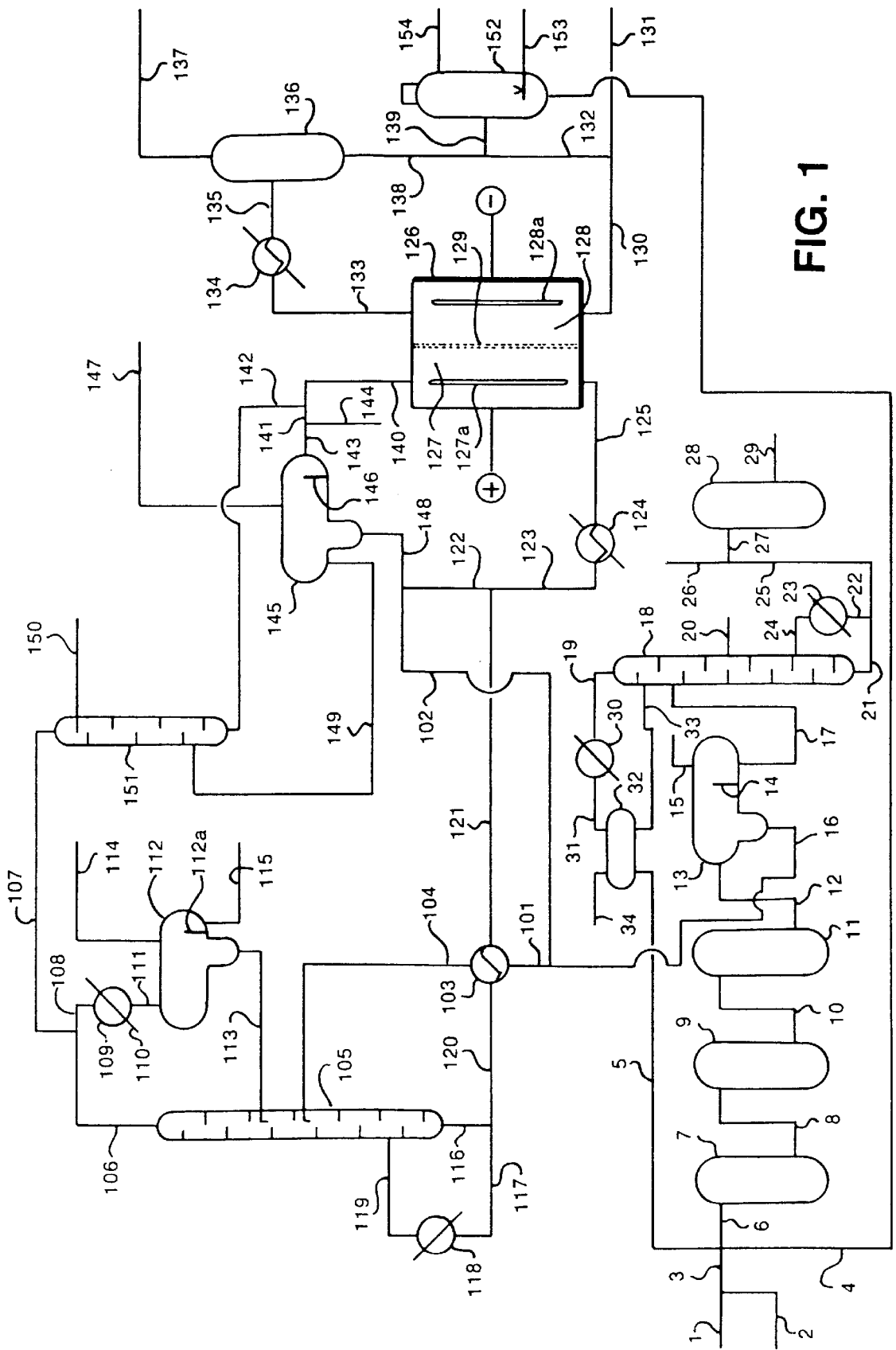

United States Patent [19]
Harrison et al.

[11] Patent Number: 5,841,002
[45] Date of Patent: Nov. 24, 1998

[54] PROCESS FOR THE COMMERCIAL PRODUCTION OF POLYHYDROXY ALCOHOLS AND GLYCOLS

[75] Inventors: George Edwin Harrison, Billericay; Arthur James Reason, Saltburn, both of United Kingdom

[73] Assignee: Davy Process Technology Limited, London, England

[21] Appl. No.: 723,186

[22] Filed: Sep. 27, 1996

[30] Foreign Application Priority Data

Sep. 28, 1995 [GB] United Kingdom ............... 9519975

[51] Int. Cl.$^6$ ............................................. C07C 31/18
[52] U.S. Cl. ........................................ 568/853; 568/854
[58] Field of Search ................................ 568/853, 854

[56] References Cited

U.S. PATENT DOCUMENTS

| | | | |
|---|---|---|---|
| 4,247,653 | 1/1981 | Wagner | 521/158 |
| 4,933,473 | 6/1990 | Ninomiya et al. | 568/862 |
| 5,434,313 | 7/1995 | Harrison et al. | 568/461 |

OTHER PUBLICATIONS

Eberson, L. in Organic Electrochemistry, ed. Baizer, M.M, 1973, Marcel Dekker, Inc., pp. 469–475.
Aldrich Catalogue, 1994, pp. 1093, 1411, 1414.

*Primary Examiner*—Alan L. Rotman
*Assistant Examiner*—Garth M. Dahlen
*Attorney, Agent, or Firm*—Rothwell, Figg, Ernst & Kurz

[57] ABSTRACT

An aldolisation process is disclosed for converting an aldehyde or mixture of aldehydes, such as iso-butyraldehyde and formaldehyde, to a desired polyhydroxy alcohol or glycol, such as neopentyl glycol. Aldolisation is effected in a stirred tank reactor using an alkali catalyst, such as sodium hydroxide. An aldolisation intermediate product is converted to the desired polyhydroxy alcohol or glycol by a hydrogenation or cross-Cannizzaro reaction step. The product is recovered and an aqueous catalyst-containing phase is recycled to the aldolisation zone. At least a portion of this catalyst recycle stream is purged to control the build up of cross-Cannizzaro products in the recycle stream. The purge stream is treated electrolytically to obtain an aqueous catalyst-containing solution for recycle to the aldolisation zone and an effluent stream comprising volatile organic materials and being substantially free from alkali catalyst.

25 Claims, 2 Drawing Sheets

PROCESS FOR THE COMMERCIAL PRODUCTION OF POLYHYDROXY ALCOHOLS AND GLYCOLS

This invention relates to a process for the production of polyhydroxy alcohols and/or glycols by one or more aldolisation reaction steps followed by at least one further reaction step including a reaction step selected from a cross-Cannizzaro reaction step and a hydrogenation step.

Aldolisation is a well known process in which two aldehyde molecules undergo condensation, typically in the presence of an alkali metal hydroxide catalyst, according to the following equation:

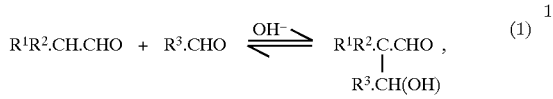
(1)

where $R^1$, $R^2$ and $R^3$ are independently, a hydrogen atom, an alkyl group or an aryl group. Provided that the aldolisation product of equation (1) has at least one α-hydrogen, i.e. provided that at least one of $R^1$ and $R^2$ is a hydrogen atom, further aldolisation can occur according to the following equation:

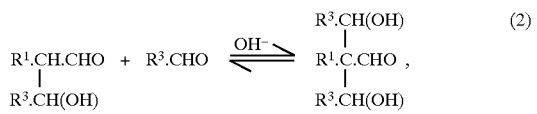
(2)

In the presence of an alkali catalyst, the condensation product aldol can undergo a cross-Cannizzaro reaction to form a glycol, according to the following equation:

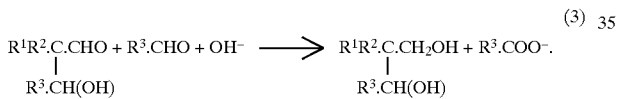
(3)

The same glycol can also be produced by hydrogenation of the hydroxyaldehyde produced by equation (1):

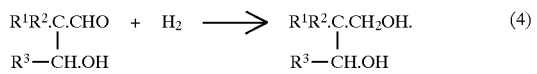
(4)

Useful aldolisation products may be formed from the reaction of aldehydes containing different numbers of carbon atoms. Of particular interest are the reactions of certain aldehydes with formaldehyde. For example, neopentyl glycol may be produced by the aldol condensation of formaldehyde with iso-butyraldehyde followed by a cross-Cannizzaro reaction between the intermediate β-hydroxyaldehyde, 2,2-dimethyl-3-hydroxypropanal, and formaldehyde, according to the following equations:

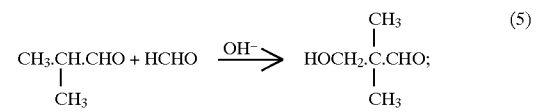
(5)

and

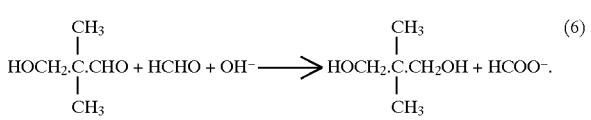
(6)

An alternative mechanism for neopentyl glycol production is described in U.S. Pat. No. ,3920,760 as follows:

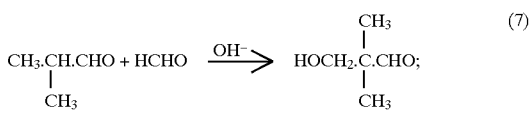
(7)

and

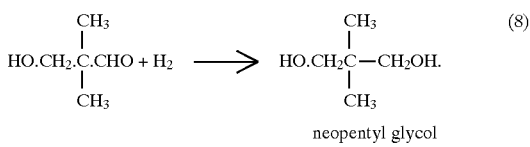
(8)

neopentyl glycol

The step of equation (7) is an aldol condensation in which the base serves as a catalyst. The step of equation (8) involves hydrogenation of the hydroxyaldehyde. This route to neopentyl glycol is also disclosed in, for example, U.S. Pat. No. 2,895,996.

If the crossed Cannizzaro reaction of equation (6) is used for the conversion of the hydroxy aldehyde product of equations (5) and (7) to the polyol, then theoretically one mole of aldehyde and one mole of base are converted to one mole of a carboxylic acid salt per mole of glycol produced.

Even if the reaction is limited to the production of hydroxyaldehyde, unwanted side reactions lead to the formation of acidic materials which consume the basic catalyst of equations (5) and (7). Some of these side reactions are shown below:

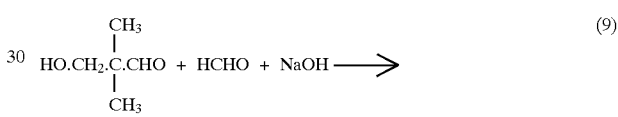
(9)

(10)

and

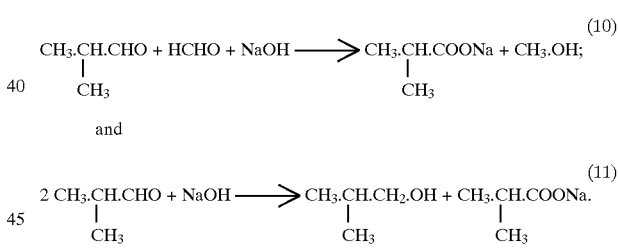
(11)

Equations (9) and (10) are examples of cross-Cannizzaro reactions, while equation (11) is an example of a Cannizzaro reaction between two molecules of the same aldehyde.

Thus, as is taught in U.S. Pat. No. 3,920,760, sodium 3-hydroxy-2,2-dimethyl-propionate (sodium hydroxypivalate) and sodium iso-butyrate are known by-products of this synthetic route to neopentyl glycol. If the final step in the production of neopentyl glycol is a cross-Cannizzaro reaction between 3-hydroxy-2,2-dimethyl-propionaldehyde, formaldehyde and sodium hydroxide, then sodium formate is also formed. Persons skilled in the art will recognise that a variety of other cross-Cannizzaro or Cannizzaro reactions may occur.

Neopentyl glycol finds application in a range of technologies, including waterborne and alkyd surface coatings, gel coatings for fibreglass-reinforced plastics, powder coatings, lube oil additives, plasticisers and polyurethanes. The aldol product is produced without any dehydration step.

1,1,1-trimethylol propane is also of value, inter alia, in the production of alkyd resin coatings and can be produced by the aldol condensation of formaldehyde with n-butyraldehyde according to the following equations:

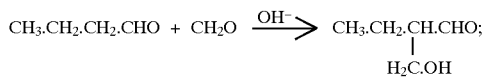 (12)

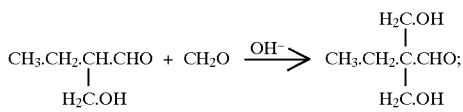 (13)

and

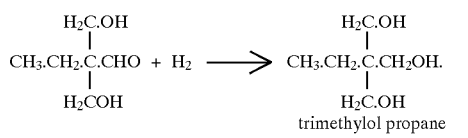 (14)

trimethylol propane

Equations (12) and (13) are both aldol condensation reactions in which $OH^-$ serves as a catalyst. Equation (14) is a hydrogenation of the dihydroxyaldehyde product of step (13).

In a way that is analogous to by-product formation in the synthesis of neopentyl glycol, sodium butyrate, sodium formate and sodium 2,2-di(hydroxymethyl)-butyrate can be formed in alkali-consuming side reactions.

The conversion of 2,2-di(hydroxymethyl)-butyraldehyde to 1,1,1-trimethylol propane can also be effected by a crossed Cannizzaro reaction using formaldehyde as the reducing agent in the presence of a basic catalyst.

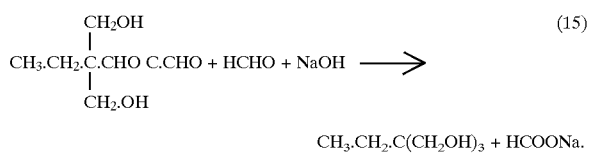 (15)

$CH_3.CH_2.C(CH_2OH)_3 + HCOONa.$

In this case at least one mole of sodium formate is formed per mole of neopentyl glycol produced.

Another important commercial chemical which finds its principal application in the surface coating industry as a raw material for oil-modified alkyd resins and synthetic drying oils is pentaerythritol. This compound can also be produced by successive aldolisation steps followed by a hydrogenation or cross-Cannizzaro step, the starting materials being acetaldehyde and formaldehyde. The reaction proceeds according to the following equations:

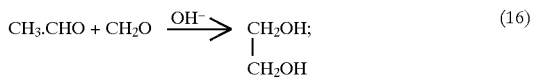 (16)

and

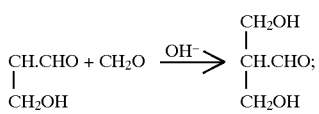 (17)

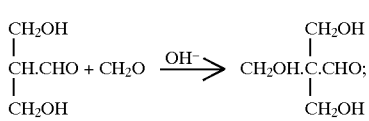 (18)

and is followed either by

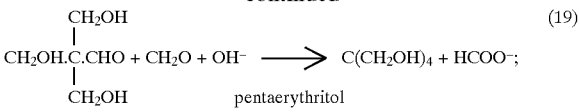 (19)

pentaerythritol or by

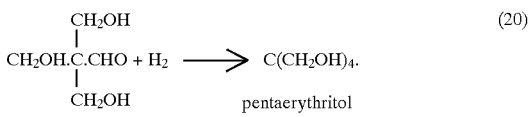 (20)

pentaerythritol

Equations (16) to (18) in the production of pentaerythritol are aldol condensations and equation (19) is a cross-Cannizzaro reaction. The final step may also be effected by hydrogenation of the trihydroxyaldehyde product of equation (18), as is shown in equation (20).

Another important commercial chemical is 2,2,4-trimethyl-1,3-pentanediol which is used inter alia as an intermediate in the production of unsaturated polyesters. This compound can be produced by aldolisation (or, as it may alternatively be termed, aldo-trimerisation) of iso-butyraldehyde followed by hydrogenation of the resulting intermediate aldolisation product, 2,6-di-iso-propyl-5,5-dimethyl-1,3-dioxan-4-ol, according to the following equations:

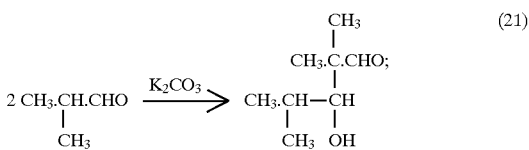 (21)

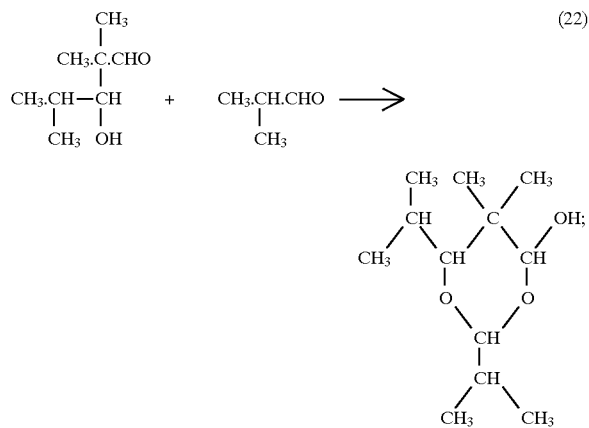 (22)

and

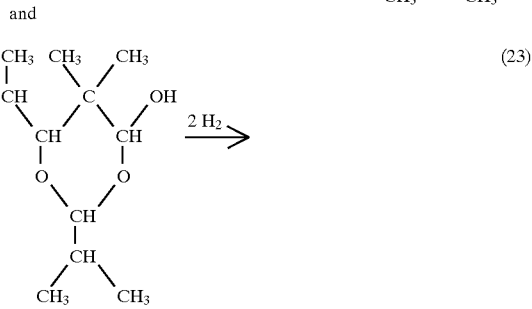 (23)

-continued

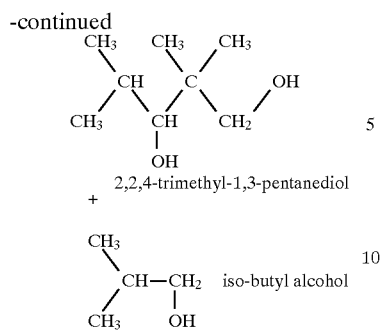
2,2,4-trimethyl-1,3-pentanediol

+

iso-butyl alcohol

Equations (21) and (22) are aldolisation steps and equation (23) is a hydrogenation step.

It has been suggested in "The Green Potential of Electrochemistry", Engineering Practice, November 1992, pages 132 to 141 by D. Pletcher and N. L. Weinberg to use electrolysis cells to treat effluents. This paper mentions the need for technology to convert sodium salts back into sodium hydroxide. Similarly, U.S. Pat. No. 4,337,126 is directed to an electrolytic process for converting alkali metal carbonates to alkali metal hydroxides. U.S. Pat. No. 3,842,157 relates to a process for producing sodium carbonate monohydrate from a sodium hydroxide solution obtained in the production of chlorine via the diaphragm cell process.

There is a need to provide an improved process for the production of polyhydroxy alcohols and glycols by one or more aldolisation steps followed by at least one hydrogenation or cross-Cannizzaro step. In particular there is a need to provide a more environmentally friendly and efficient process for the production of polyhydroxy alcohols and glycols.

The present invention accordingly seeks to provide a novel, improved process for the production of polyhydroxy alcohols or glycols by condensation of saturated aldehydes through aldolisation to form an intermediate aldolisation product followed by subjection of the intermediate aldolisation product to at least one further step including a step selected from hydrogenation or cross-Cannizzaro reaction. It further seeks to provide such a process whereby the quantity of alkaline effluent, or at least of metal values from the aldolisation catalyst, which is discharged from the plant can be reduced to a low level, preferably to a level at or around zero.

The invention provides a process for the production of a compound having the formula:

$$\underset{R^3}{\overset{R^1 \quad R^2 \quad R^4}{HO-CH-C-CH-OH,}} \qquad (I)$$

in which $R^1$ and $R^4$ each represent, independently of the other, a hydrogen atom, an alkyl group, an aralkyl group, or an aryl group; and $R^2$ and $R^3$ each represent, independently of the other, an alkyl group, a hydroxyalkyl group, an aralkyl group, an arylhydroxyalkyl group, or an aryl group; which process comprises:

(a) reacting one mole of a first aldehyde having at least one α-hydrogen atom and having the formula:

in which $R^5$ is a hydrogen atom, an alkyl group, an aralkyl group, or an aryl group; and $R^6$ is a hydrogen atom, an alkyl group, an aralkyl group, or an aryl group; with at least one mole of a second aldehyde having the formula:

$$R^7—CHO \qquad (III),$$

in which $R^7$ is a hydrogen atom, an alkyl group or an aryl group; under aldolisation conditions in the presence of an aldolisation catalyst selected from alkali metal hydroxides, alkali metal carbonates, alkali metal bicarbonates, and mixtures thereof, and from alkaline earth metal hydroxides and mixtures thereof with alkali metal hydroxides, thereby to generate an intermediate aldolisation product;

(b) converting the intermediate aldolisation product of step (a) by one or more further steps including a step selected from hydrogenation and a cross-Cannizzaro reaction to the compound having the formula (I);

(c) recovering the compound having the formula (I);

(d) recovering an aqueous spent catalyst phase containing metal values and at least one Cannizzaro or cross-Cannizzaro reaction product or by-product;

(e) passing material of the spent catalyst phase to an electrolysis zone comprising an anode zone containing an anode, a cathode zone containing a cathode, and at least one ion selective barrier means separating the anode zone from the cathode zone;

(f) passing a direct current or rectified alternating current between the anode and the cathode thereby to liberate metal hydroxide in the cathode region, said metal hydroxide being selected from alkali metal hydroxides, alkaline earth metal hydroxides, and mixtures thereof;

(g) recovering liberated metal hydroxide of step (f);

(h) if necessary, converting at least a portion of the liberated metal hydroxide of step (g) to the catalyst of step (a); and (i) recycling at least one of liberated metal hydroxide of step (g) and converted metal hydroxide of step (h) for use as aldolisation catalyst in step (a).

Conveniently step (g) may comprise the steps of:

(j) recovering from the anode region of said electrolysis zone a liquid phase and gas phase;

(k) separating said liquid phase and said gas phase;

(l) steam stripping at least a portion of said liquid phase;

(m) recovering from said stream stripping step (1) an overhead fraction;

(n) condensing said overhead fraction to provide a condensed liquid phase comprising water and steam volatile organic compounds in a form substantially free of said aldolisation catalyst; and (o) recovering condensed liquid phase from said overhead fraction for recycle to the anode region of said electrolysis zone.

In one preferred process there is provided an aldolisation zone and a hydrogenation zone in which conversion of the intermediate aldolisation product to the desired polyhydroxy alcohol or glycol is effected by a hydrogenation reaction.

In another process according to the invention, conversion of the intermediate aldolisation product to the desired polyhydroxy alcohol or glycol is effected by a cross-Cannizzaro reaction between the intermediate aldolisation product, said second aldehyde and said catalyst. In this case there can be provided an aldolisation zone in which both the initial aldolisation and the cross-Cannizzaro reaction take place.

In one preferred process according to the invention said at least one ion selective barrier means is permeable to cations from said aldolisation catalyst, the materials of the spent catalyst stream being supplied to the anode region of said electrolysis zone. Preferably in this case an aqueous phase comprising water is supplied to the cathode region of said electrolysis zone. This aqueous phase may further comprise an electrolyte in order to maintain electrical conductivity in the electrolysis zone. Conveniently, the electrolyte is supplied as a portion or the alkali metal hydroxide liberated in the cathode region of said electrolysis zone. Barrier means suitable for use in this process include cation exchange membranes such as the perfluorinated membranes having cation exchange groups such as groups selected from sulphonic acid groups, sulphonamide groups, and carboxylic acid groups as substituents for example, the materials sold as Nafion (1000 series), which has sulphonic acid substituents, Nafion Sulfonamide, which has sulphonamide substituents, and Nafion 901, which has carboxylic acid and sulphonic acid substituents. These materials are sold by E. I. duPont de Nemours, Wilmington, Del. Alternatively it may be made from Aciplex, which has sulphonic acid groups, or Flemion Selemion, which has carboxylic acid substituents, sold by Asahi Limited. Another material that can be used for the membrane is Neosepta-F or Neosepta, which contain carboxylic acid and sulphonic acid substituents, sold by Tokuyama Soda. (The words "Nafion", "Aciplex", "Flemion Selemion" and "Neosepta" are Trade Marks.)

In another process according to the invention, said at least one ion selective barrier means is permeable to anions of the type comprising the at least one Cannizzaro reaction by-product, the material of the spent catalyst stream being supplied to the cathode region of said electrolysis zone. An aqueous phase comprising water can be supplied to the anode region of said electrolysis zone. This aqueous phase may further comprise an electrolyte in order to maintain electrical conductivity in the electrolysis zone. Conveniently, the electrolyte comprises alkali metal hydroxide liberated in the cathode region of said electrolysis zone. Barrier means suitable for use in this process include perfluorinated anion exchange membranes having groups such as amino groups or quaternary ammonium groups available for anion exchange.

In yet another process in accordance with the invention, at least two barrier means are employed, a first one of the at least two barrier means being permeable to cations and a second one of the at least two barrier means being permeable to anions. In this case the electrolysis zone comprises a cathode region separated from an intermediate region by said first barrier means and an anode region separated from said intermediate region by said second barrier means. The material of the spent catalyst stream is supplied to the intermediate region of said electrolysis zone. Optionally, an aqueous phase comprising water is supplied to one or both of the cathode and anode regions of said electrolysis zone. This aqueous phase may further comprise an electrolyte in order to maintain electrical conductivity in the electrolysis zone. Conveniently, the electrolyte comprises alkali metal hydroxide liberated in the cathode region of said electrolysis zone.

Accordingly, the invention provides an improved aldolisation process wherein the spent catalyst phase, or a portion thereof, is subjected to electrolysis under conditions which substantially facilitate the removal of Cannizzaro and cross-Cannizzaro products from the spent catalyst phase by the Kolbe reaction and by the production of free carboxylic acids and which regenerate the aldolisation catalyst or a precursor thereto for recycle to the aldolisation step.

The Kolbe reaction was first carried out in 1849 and has been used since in organic synthesis. Among the simplest materials to undergo the Kolbe reaction when electrolysed are carboxylic acids. An acid of general formula RCOOH where R is a hydrogen atom, an alkyl group or an aryl group will reversibly dissociate to yield hydrogen ions and ions of formula RCOO$^-$. Generally the Kolbe reaction is carried out in the presence of sodium or potassium carboxylate salts because many carboxylic acids are only weakly ionised and are therefore poor conductors of electricity. These anions will, on electrolysis under suitable conditions, lose an electron to form free radicals of formula RCOO·. These radicals are unstable and undergo decarboxylation to form R· and $CO_2$, thereby liberating carbon dioxide at the anode. Two R· radicals can unite to yield a compound of formula R—R. Other compounds may also be synthesised under the Kolbe reaction conditions. For example, in aqueous solution OH$^-$ ions will be present and on discharge will form HO· radicals which can combine with R· radicals to produce alcohols of formula R—OH. The hydroxyl radicals can also participate in the oxidation of the organic compounds via hydrogen abstraction reactions, addition to double bonds, and combination with organic radicals. Reactions of this type are believed to be responsible for the removal of heavy but non-ionisable materials in the anode region. The reaction $$2HO· \rightarrow H_2O_2 \rightarrow H_2O + \tfrac{1}{2}O_2 \qquad (20)$$

is believed to be at least partially responsible for the formation of oxygen in the anode region.

Esters formed by the joining of R· and RCOO·, i.e. RCOOR, hydrocarbons of formula RH, and olefins of formula containing one less hydrogen atom than R· are also products under the Kolbe reaction conditions. Peroxy compounds of the formula HOOH, ROOH or ROOR may also be formed by free radical combination under certain conditions.

In an electrolytic cell with anode and cathode regions the free carboxylic acid can be formed by the transfer of alkali metal ions through a membrane dividing the regions.

(21)

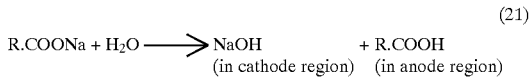

R.COONa + H$_2$O ⎯⎯→ NaOH + R.COOH
(in cathode region) (in anode region)

The application of the Kolbe reaction and of other reactions which can occur under the Kolbe reaction conditions in organic synthesis has been extensively reported and reviewed, for example in:

1) Svadkovskaya, G. E. and Voitkevich, S. A., "Electrolytic Condensation of Carboxylic Acids" in Russian Chemical Reviews, 29(3), 1960, pages 161 to 167;
2) Koehl, W. J., "Anodic Oxidation of Aliphatic Acids at Carbon Anodes" in Journal of the American Chemical Society, 1964, pages 4686 to 4690; and
3) Eberson, Lennart, "The Chemistry of Carboxylic Acids", Interscience, 1969, pages 54 to 99.

According to the afore-mentioned article by Svadkovskaya, G. E. and Voitkevich, S. A., the anode material has an effect on the course of the reaction in the electrolysis cell. Thus it was reported that in the electrolysis of acetates the highest yields of ethane were obtained using a smooth platinum or iridium anode, while gold, nickel and platinised platinum anodes gave negative results. On the other hand graphite anodes gave moderate yields of ethane.

In the process of the invention it is accordingly preferred to use an anode made of a material that promotes the Kolbe reaction. Thus it is preferred to use smooth platinum or iridium anodes. Conveniently the cathodes are also smooth platinum electrodes.

The Kolbe reaction is not limited to carboxylic acids. Alkali metal carboxylates will also undergo electrolytic decomposition according to the mechanism outlined briefly above and reported fully in the literature. Generally the Kolbe reaction is carried out in aqueous solution containing free carboxylic acid and the corresponding alkali metal salt of the acid.

In conventional aldolisation processes, it is both cost effective and environmentally friendly to recycle the alkali catalyst, which is usually sodium hydroxide, to the aldolisation zone. However, in processes involving one or more cross-Cannizzaro steps, either as side reactions or especially as the means of converting the intermediate hydroxy or polyhydroxy aldehyde to the desired polyhydroxy alcohol or glycol, the alkali catalyst is chemically consumed and converted to a major by-product salt, typically sodium formate. This reaction itself consumes valuable catalyst which must then be replaced at extra cost to the operator of the process. The by-product salt must also be recovered, purified and sold or sent to other means of disposal. This generally imposes extra capital and operating costs on the polyol producer in terms of the isolation, purification or disposal of the by-product salt. Market demand for such by-product salts rarely compares favourably with the relative costs and rates of production by this process. Also, as the aqueous catalyst stream is recycled, the proportion by weight of cross-Cannizzaro products contained therein increases. A high proportion of such products in the aldolisation catalyst recycle stream reduces the efficiency of the aldolisation catalyst. Accordingly, the catalyst recycle stream must be purged from time to time to control the build up of cross-Cannizzaro products.

In U.S. Pat. No. 3,920,760 the aqueous aldolisation catalyst containing stream is discharged from the plant after a single pass through the aldolisation reactor. The disposal of this alkaline purge stream or, in the case of U.S. Pat. No. 3,920,760, the discharged aqueous stream adds process operating and capital costs both in terms of the valuable catalyst lost in the purge and in terms of the expense of treating the alkaline purge stream to reduce its chemical and biological oxygen demand (COD and BOD) before it can safely be discharged to the environment.

The COD and BOD criteria for such discharge as well as for the allowable metal contents such as alkali metal content, are becoming increasingly more stringent. The present invention provides a process involving aldolising an aldehyde for production of a polyhydroxy alcohol or glycol in which the build up of Cannizzaro or cross-Cannizzaro products is controlled by electrolytic treatment of at least a portion of the catalyst recycle stream.

The invention further provides a process for the production of polyhdroxy alcohols and glycols which comprises the steps of:

(A) subjecting at least one aldehyde to aldolisation conditions in the presence of an effective amount of an aldolisation catalyst selected from alkali metal hydroxides, alkali metal carbonates, alkali metal bicarbonates and mixtures thereof, and from alkaline earth metal hydroxides and mixtures thereof with alkali metal hydroxides to form a desired aldol intermediate;

(B) converting said aldol intermediate by means of at least one further reaction step including a reaction step selected from a hydrogenation reaction and a cross-Cannizzaro reaction to form at least one polyhydroxy alcohol or glycol;

(C) recovering from the aldol intermediate conversion step (B) a reaction mixture comprising unreacted aldehyde or aldehydes, water, aldolisation catalyst, at least one polyhydroxy alcohol or glycol, and at least one Cannizzaro or cross-Cannizzaro reaction product;

(D) separating from the reaction mixture a first aqueous phase comprising water, aldolisation catalyst and at least one Cannizzaro or cross-Cannizzaro reaction product;

(E) supplying at least a portion of said first aqueous phase to an electrolysis zone;

(F) electrolysing said portion of said first aqueous phase in said electrolysis zone to generate electrolysis products, including a metal hydroxide selected from said alkali metal hydroxide and said alkaline earth metal hydroxide;

(G) recovering from a cathode region of said electrolysis zone a second aqueous phase, the concentration of said at least one Cannizzaro or cross-Cannizzaro product in said second aqueous phase being below that in said first aqueous phase, said second aqueous phase comprising water and said metal hydroxide;

(H) if necessary converting said metal hydroxide of step (G) to the catalyst of step (A); and (I) supplying to the aldolisation step as catalyst for step (A) a material selected from the metal hydroxide of step (G) and the converted metal hydroxide of step (H).

Preferably in step (E) any remaining portion of said first aqueous phase is recycled to said aldolisation step.

If said first portion of said first aqueous phase is supplied to the anode region of said electrolysis zone then, optionally, an aqueous phase comprising water is supplied to the cathode region of said electrolysis zone to control the concentration of the alkali metal or alkaline earth metal hydroxide recovered from the cathode region of said electrolysis zone. This aqueous phase may be distilled or deionised water or may be a solution of the alkali metal or alkaline earth metal hydroxide.

The invention provides substantial advantages over conventional aldolisation processes. In the process of the invention the Cannizzaro and any cross-Cannizzaro reaction by-product salts, some of which are generally non-volatile and difficult to purge from the system without consequential loss of aldolisation catalyst metal values, are converted to alkali metal hydroxide, alkaline earth metal hydroxide, or a mixture thereof, as the case may be, and to metal-free organic products. Typically the electrolysis step is conducted so as to promote the Kolbe reaction. In this case the Cannizzaro and any cross-Cannizzaro reaction by-product salts are converted to alkali metal hydroxide and/or alkaline earth metal hydroxide and to extractable or relatively volatile products by the Kolbe reaction. If the Cannizzaro product has the formula RCOOM, where M is an alkali metal ion or $(RCOO)_2M$ where M is an alkaline earth metal ion, then the Kolbe reaction products will comprise $CO_2$, R—R, RH and R—OH, all of which will generally be relatively volatile compounds removable from the plant by conventional methods such as flaring, steam stripping, or gaseous discharge. In some cases solvent extraction may be an appropriate method of recovering the Kolbe reaction products. For example, in a process for producing neopentyl glycol, by aldolising in the presence of a sodium hydroxide catalyst a mixture of formaldehyde and iso-butyraldehyde, the Cannizzaro reaction salt products will include sodium formate, sodium 3-hydroxy-2,2-dimethylpropionate and sodium iso-butyrate. After electrolysis, the anions from these compounds will be converted to Kolbe products, including carbon dioxide, water, hydrogen, 2,3- dimethylbutane and 2,2,3,3-tetramethylbutane-1,4-diol. Similarly, a process for producing trimethylol propane by aldolising n-butyraldehyde and formaldehyde in the presence of a sodium hydroxide catalyst will yield sodium formate, sodium butyrate and sodium 2,2-di (hydroxymethyl)-butyrate as cross-Cannizzaro products. The corresponding Kolbe products will include carbon dioxide, water, hydrogen, 3,3,4,4-tetra-(hydroxymethyl)-hexane and hexane. It will be apparent to the skilled person that all the aforementioned Kolbe products are relatively volatile compounds, when compared with the Cannizzaro product or products from which they are respectively formed. The polyhydroxy Kolbe products, although high boiling materials, are not acidic and are therefore capable of being extracted from the aqueous phase by organic solvents, such as the hexane formed in the above-mentioned reaction.

The invention requires the use of an electrolysis zone in which to convert Cannizzaro products to electrolysis products and to regenerate an alkali metal or alkaline earth metal hydroxide for use as, or conversion to, aldolisation catalyst for recycle to the aldolisation step. The electrolysis zone comprises a vessel in which to receive the stream to be electrolysed, an anode means, a cathode means and means to supply a direct or rectified alternating current to the electrolysis zone. A barrier means selectively permeable to anions and/or cations, for example an ion permeable membrane separates the anode region from the cathode region. In some applications, the anode and cathode regions may be separated by a porous diaphragm. The membrane or diaphragm is preferably permeable to cations such as sodium or other alkali metal ions or alkaline earth metal ions. In this way, the anode region of the electrolysis zone is separated from the cathode region thereof by the membrane or other ion-permeable barrier means. The stream to be electrolysed is, in this case, supplied to the anode region of the electrolysis zone. Water is optionally supplied to the cathode region. When a direct or rectified alternate current is applied, negative ions such as carboxylate ions and hydroxide ions present in the purge stream are oxidised at the anode and positive ions such as sodium ions move through the membrane to the cathode where, if the cation is a sodium ion, sodium hydroxide is formed.

However, it is also within the scope of the invention to use a membrane or diaphragm which is permeable to anions. In this case, the purge stream to be electrolysed is supplied to the cathode region of the electrolysis zone. Water is optionally supplied to the anode region. When a direct or rectified alternating current is applied, positive ions such as alkali metal or alkaline earth metal ions present in the purge stream move towards the cathode where they combine with hydroxide ions produced at the cathode by the discharge of hydrogen ions from electrolysed water and negative ions such as are present in the Cannizzaro product or products move through the membrane to the anode where they are oxidised to Kolbe products. If desired, a source of metal ions, such as sodium ions, can be introduced into the anode zone in order to maintain a sufficient conductivity throughout the electrolysis zone.

In the process of the invention there is used a first aldehyde of formula (II) containing at least one α-hydrogen atom or a mixture of such an aldehyde with an aldehyde of formula (III), containing one or more α-hydrogen atoms or no α-hydrogen atom. The aldehyde of formula (III) is often different from, but may be the same as, the aldehyde of formula (II). Examples of aldehydes containing at least two α-hydrogen atoms include acetaldehyde, propionaldehyde, n-butyraldehyde, n-valeraldehyde, 3-methylbutyraldehyde, n-hexanal, β-phenylacetaldehyde, n-heptanal, n-octanal, n-decanal, and the like. Examples of aldehydes containing a single α-hydrogen atom are 2-methylpropionaldehyde, 2-methyl-butyraldehyde, 2-ethylhexanal, 2-methyl-3-phenyl-propionaldehyde, and the like. Examples of aldehydes containing no α-hydrogen atoms are formaldehyde, p-tolualdehyde, [2,2,2]-bicyclooctane-1-aldehyde, [2,2,1]-bicycloheptane-1-aldehyde, pivaldehyde, 1-methylcyclohexane-1-aldehyde, benzaldehyde, and the like.

The aldolisation catalyst preferably comprises an alkali metal hydroxide, bicarbonate or carbonate, or a mixture of two or more thereof, or an alkaline earth metal hydroxide or a mixture thereof with an alkali metal hydroxide. The aldolisation catalyst is normally present in the aldolisation zone in aqueous solution. Preferably the aldolisation catalyst is selected from sodium hydroxide, sodium carbonate, potassium hydroxide, potassium carbonate, and a mixture of two or more thereof. Other suitable aldolisation catalysts include lithium, rubidium and caesium hydroxides and carbonates, and calcium, strontium and barium hydroxides. In conventional aldolisation processes expensive catalysts such as rubidium and caesium hydroxides are infrequently used because of the cost of replacing the portion of catalyst lost in the Cannizzaro product purge stream. Because the present invention provides an aldolisation process wherein loss of cations present in the aldolisation catalyst from the plant can be reduced substantially to zero, it is commercially practicable to utilise, if desired, those aldolisation catalyst hitherto neglected on grounds of cost. The invention therefore allows the aldolisation plant operator considerable freedom to select the most favourable catalyst for the particular aldolisation or aldolisations being performed.

The concentration of aldolisation catalyst in the aqueous phase in the aldolisation zone typically ranges from about 0.1% w/v up to about 15% w/v or more, e.g. up to about 20% w/v or higher. Under normal circumstances, however, the concentration of aldolisation catalyst in the aqueous phase ranges from about 0.1% w/v up to about 10% w/v.

The aldolisation zone is typically maintained at a temperature in the range of from about 0° C. up to about 180° C. or higher, preferably in the range of from about 10° C. to about 150° C. The operating pressure of the aldolisation zone can vary within fairly wide limits. This pressure is determined by the temperature and composition of the organic and aqueous phases in the aldolisation zone, if a vapour phase is present. If the aldolisation zone is full of liquid, then any desired pressure can be imposed. Operating pressures in the aldolisation zone typically range from about 0.1 bar up to about 20 bar or higher, e.g. from about 0.5 bar to about 10 bar.

An aldehyde or aldehydes is or are supplied to the aldolisation zone, in addition to aqueous alkali catalyst-containing solution. Such aldehyde can comprise feed aldehyde (or make up aldehyde) and recycled aldehyde. The ratio of recycled aldehyde to feed aldehyde can range, for example, from about 5:1 to about 1:50 by volume. Typically the ratio is from about 1:1 to about 1:20.

The aldehyde residence time in the aldolisation zone is typically from about 1 minute up to about 150 minutes or more, normally at least 2 minutes, e.g. from about 5 minutes to about 75 minutes.

If there is present in the aldolisation zone an organic and an aqueous phase then these are dispersed one in the other. Generally any static or dynamic mixing method that provides the required degree of dispersion of the phases one in the other can be used.

The aldolisation zone may comprise a static mixing zone. Alternatively, however, at comprises a vessel, optionally fitted with internal baffles, fitted with an impeller. Since the rate of reaction appears to depend strongly upon the interphase area, due to the need for the aldehyde to cross the aqueous phase-organic phase interface in order to come into contact with the alkali catalyst, it is desirable to agitate the two phases vigorously so as to form a liquid-liquid dispersion. Preferably this liquid-liquid dispersion is an aqueous-continuous dispersion so that the dispersion is of the oil-in-water type. This can usually be achieved, when using an impeller, by ensuring that the impeller is in the aqueous phase at start up. Typically the power supplied to the impeller ranges from about 0.5 to about 5.0 kW/m$^3$ of liquor, e.g. from about 1.0 to about 3.0 kW/m$^3$ of liquor.

In some cases the reactants and the products form a homogeneous single phase mixture. However, in those cases in which two distinct liquid phases are present and a dispersion is formed in the aldolisation zone, the organic phase:aqueous phase ratio typically ranges from about 15:1 to about 1:15 by volume, e.g. from about 5:1 to about 1:5 by volume.

The conditions for effecting Cannizzaro and cross-Cannizzaro reactions are typically the same as those used in the aldolisation step. However, if desired, higher temperatures and/or higher pressures may be used in the conversion step (b), where this comprises a cross-Cannizzaro reaction step, than in the aldolisation step.

If the conversion step (b) comprises a hydrogenation step, then the hydrogenation conditions which are selected will typically be those appropriate for hydrogenation of an aldehyde. Such hydrogenation conditions include use of a hydrogenation catalyst, such as nickel or reduced copper oxide/zinc oxide, as well as a reaction temperature in the range of from about 45° C. to about 240° C. and a pressure in the range of from about 1 bar to about 50 bar.

Figure 2:
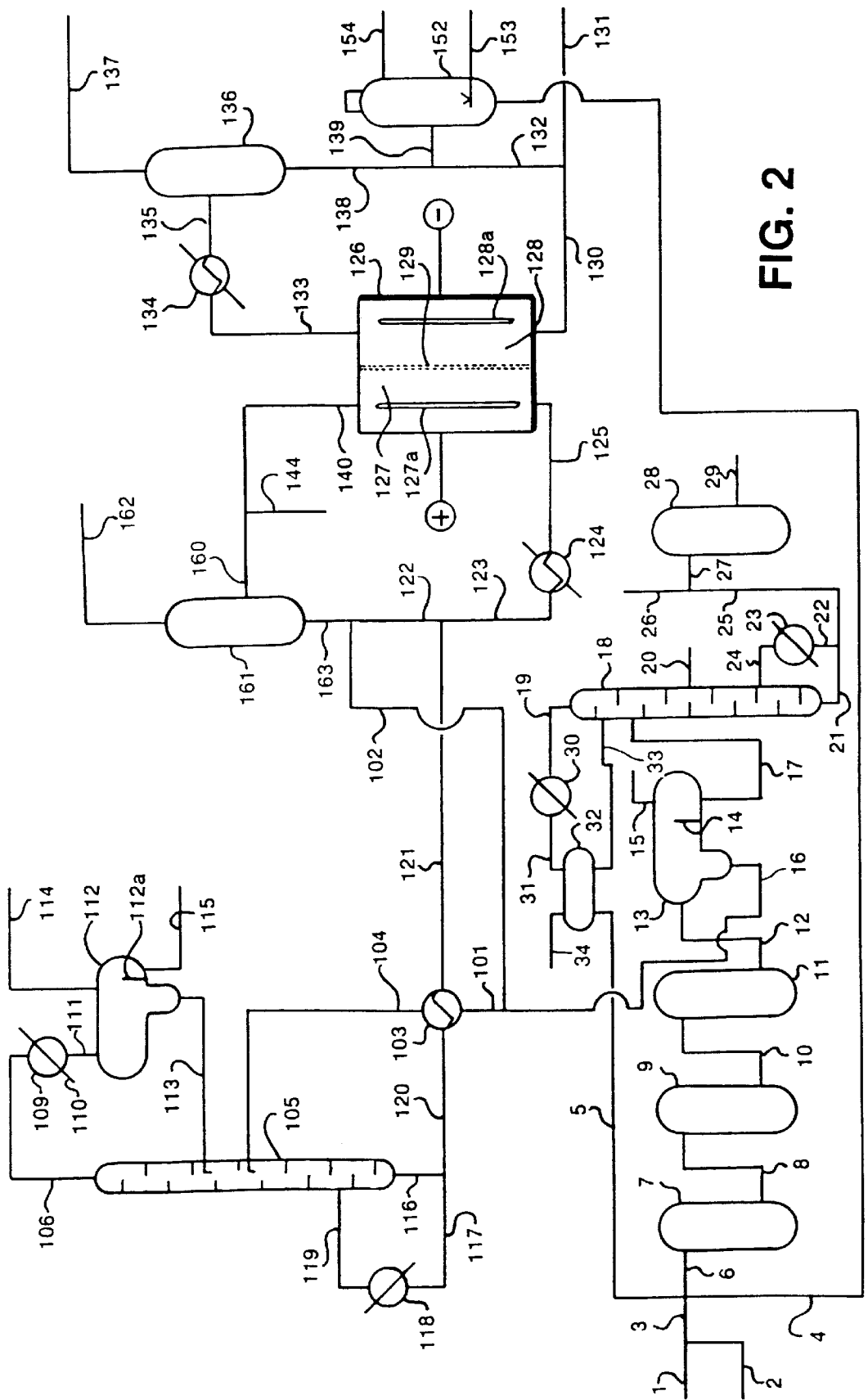

In order that the invention may be clearly understood and readily carried into effect a first preferred process in accordance therewith will now be described, by way of example only, with reference to the accompanying drawings wherein:

FIG. 1 is a flow diagram of the effluent treatment stage of a plant for the production of neopentyl glycol by condensation of formaldehyde and iso-butyraldehyde; and FIG. 2 is a flow diagram of an alternative effluent treatment stage of a plant for the production of neopentyl glycol by condensation of formaldehyde and iso-butyraldehyde.

It will be appreciated by those skilled in the art that, as the drawing is diagrammatic, many items which would be required in accordance with conventional practice on a commercial plant, such as valves, pressure control valves, temperature sensors, pressure sensors, temperature controllers, pressure controllers, pumps, coolers, heat exchangers, and the like, have been omitted for the sake of clarity. The provision of such conventional items of equipment forms no part of the present invention. Such items would be fitted in accordance with normal chemical engineering practice.

Referring to FIG. 1, there is illustrated a plant for the production of neopentyl glycol by reaction of iso-butyraldehyde with formaldehyde in the presence of sodium carbonate as aldolisation catalyst to form the β-hydroxyaldehyde, 2,2-dimethyl-3-hydroxypropanal (hydroxypivaldehyde) according to equation (7) above. This β-hydroxyaldehyde is then subjected to hydrogenation in the presence of a Raney nickel catalyst to form neopentyl glycol according to equation (8) above.

Iso-butyraldehyde is supplied to the plant in line 1 and formaldehyde in line 2. The mixed aldehydes stream flows on in line 3 and is admixed with a recycle stream of sodium carbonate solution supplied in line 4 and with a recycle stream of iso-butyraldehyde in line 5. The resulting reaction mixture flows on in line 6 to first aldolisation stage 7. Although first aldolisation stage 7 has been depicted as a tank reactor, any other desired form of aldolisation reactor can be used, for example, a pumped loop reactor. The temperature in first aldolisation stage is typically about 70° C. and the pressure is conveniently at or just above atmospheric pressure. Preferably reactor 7 is blanketed with an inert gas, such as nitrogen.

It will normally be preferred to feed the reactants to the first aldolisation stage in a molar proportion of iso-butyraldehyde to formaldehyde of approximately 2:1, e.g. about 2.2:1.

The reaction mixture exiting first aldolisation stage 7 in line 8 is fed to a second aldolisation stage 9. Again, although second aldolisation stage has been depicted as a tank reactor, any convenient form of reactor can be used. The reaction conditions in second aldolisation stage 9 are typically substantially the same as in the first aldolisation stage 7.

From the second aldolisation stage 9 the resulting reaction mixture flows on in line 10 to a third aldolisation stage 11 of any convenient design, for example, a tank reactor. The final aldolisation product mixture emerges from third aldolisation stage 11 in line 12 and is supplied to a decanter 13 which is provided with an internal weir 14 and with a vent line 15. The spent aqueous catalyst-containing phase is recovered in line 16 for further treatment as will be described below, while the organic phase, which has overflowed weir 14 is fed in line 17 to an iso-butyraldehyde stripping column 18 from which unreacted iso-butyraldehyde is recovered overhead as a vapour in line 19 for recycle. Water is supplied to column 18 in line 20. An approximately 50:50 w/w mixture of 2,2-dimethyl-3-hydroxypropanal (hydroxypivaldehyde) and water is recovered from the bottom of column 18 in line 21. Part of the stream in line 21 is returned to the column by way of line 22, reboiler 23, and line 24. The remainder is passed on in line 25 and admixed with hydrogen from line 26. The resulting mixture flows on in line 27 to hydrogenation reactor 28 which contains a charge of Raney nickel hydrogenation catalyst. The resultant neopentyl glycol-containing stream is passed forward in line 29 for product recovery.

The overhead vapour stream in line 19 is passed to a condenser 30. The resulting condensate in line 31 is collected in a condensate receiver 32, from which a reflux stream is returned to column 18 in line 33. The remainder forms the recycle stream in line 5. Reference numeral 34 represents a vent line.

The spent aqueous catalyst-containing stream in line 16 passes on to line 101. Also supplied to line 101 is a recycle stream from line 102.

The recycle stream in line 102 also contains water, sodium hydroxide, cross-Cannizzaro products and volatile organic materials. The combined stream in line 101 is heated through exchanger 103, and is supplied via line 104 to a steam stripper 105. The steam stripper 105 removes volatile organic materials such as n-butanol and 2-methylpropanol overhead in line 106. The materials in line 106 are combined with a stream of organic material, including heavies, from line 107 and pass in line 108 through condenser 109 which is cooled by cooling water in line 110. The condensed stream passes through line 111 before entering decanter 112 which is fitted with an internal weir 112a. An aqueous phase is recycled via line 113 to reflux in the steam stripper column 105. Gaseous materials such as $CO_2$ and highly volatile organic materials are vented through line 114. An organic phase overflows weir 112a and is purged from the plant via line 115.

From the bottom of steam stripper 105 is removed, in line 116, a stream comprising an aqueous solution of sodium carboxylates and sodium hydroxide. Part of the stream is recycled to the steam stripper in line 117 through column reboiler 118 and line 119. The remainder of the steam stripper stream in line 116 is supplied in line 120 to interchanger 103 where it is cooled. The cooled stream passes on in line 121 and is combined with a stream from line 122 before being supplied via line 123 to cooler 124. This cooled stream continues in line 125 to electrolysis zone 126.

The electrolysis zone 126 comprises an anode region 127 containing an anode 127a and a cathode region 128 containing a cathode 128a separated by a membrane 129 which is permeable to sodium ions. Nafion™ is one suitable membrane. (Nafion is a trade name of E. I. du Pont de Nemours, a Corporation of Wilmington, Del.)

The stream in line 125 is supplied to the anode region 127. A stream of dilute aqueous catalyst solution is supplied to the cathode region 128 in line 130. The material in line 130 is comprised of deionised water supplied in line 131 and catalyst solution from line 132. A direct or rectified alternating current is supplied to the electrolysis zone 126 causing sodium ions present in the anode region 127 to migrate across the membrane 129 towards the cathode region 128, where they combine with hydroxide ions produced at the cathode by the discharge of hydrogen ions (i.e. electrolysis of water). Typically the voltage is from about 4 to about 12 volts and the current is from about 100 to about 5000 amp/m$^2$ amperes.

Water from line 131 is supplied as necessary via line 130 to the cathode region 128 to limit and control the concentration of the sodium hydroxide solution produced. Some water present in the stream supplied to the anode region passes through membrane 129 in association with the migrating sodium ions. A substantially pure solution of sodium hydroxide is thereby produced in the cathode region. Hydrogen gas is also liberated at the cathode through the electrolysis of water. The sodium hydroxide solution/hydrogen gas mixture is removed from the electrolysis zone 126 in line 133, cooled in exchanger 134 and supplied via line 135 to gas/liquid separator 136 where the hydrogen gas separates and is vented from the system via lines 137 and 138. Substantially pure sodium hydroxide solution exits gas/liquid separator 136 in line 138. Part is taken in line 139 for a purpose which will be further explained below. Another portion of the stream in line 138 is recycled via line 132 joining the water supplied in line 131 and continues in line 130 to cathode region 128. The recycle of this solution via line 130 serves to keep up the velocity of the liquid through cathode region 128 and sweep gas bubbles off the cathode surface.

Leaving the anode region 127 of the electrolysis zone in line 140 is a mixture of organic materials produced by the electrolysis of cross-Cannizzaro products, carbon dioxide, water, sodium hydroxide, hydrocarbons and heavies. Under some operating circumstances sodium hydroxide can be absent and free carboxylic acids can be present. A small amount of free oxygen can be generated in the anode region. This mixture is supplied to line 141 after admixture with material from line 142 and the combined stream continues in line 143, after admixture with a gas stream from line 144. The admixed steam is supplied to decanter 145 which has an internal weir 146. The gas stream in line 144 is optional and could be air (in which case the gas mixture in the ullage space of decanter 145 and line 147 would be above the upper explosive limit) or a gas such as methane (in which case the gas mixture in the ullage space of decanter 145 and line 147 would be below the lower explosive limit). This gas stream serves to keep the composition of the gases in line 147 away from the explosive compositions between the upper and lower explosive limits.

From decanter 145 an aqueous phase is recovered in line 148, comprising water, electrolysed cross-Cannizzaro products, some organic materials and optionally sodium hydroxide or carboxylic acids. Part of this stream is recycled in line 102 to steam stripper 105. Another portion of the stream in line 148 optionally passes via line 122 into line 123. This stream is then supplied to heat exchanger 124 and to the anode region 127 of electrolysis zone 126. The recycle of this stream from line 122 serves to keep up the velocity of the liquid through anode region 127 and sweep gas bubbles off the anode surface. Gases are removed from the system, leaving decanter 146 via line 147. The remaining organic materials, including heavies, overflow weir 146a and are taken in line 149 and, after washing with water from line 150 to remove sodium compounds in column 151, pass through line 107 to decanter 112. The aqueous fluid from column 151, comprising aqueous sodium compounds and some organic materials, is recycled to decanter 146 via line 143, 142 and 144.

The sodium hydroxide solution stream in line 139 is supplied to a carbonation reactor 152 in which the sodium hydroxide is converted to sodium carbonate by reaction with carbon dioxide supplied via line 153. Any necessary make-up quantities of sodium carbonate can be added to carbonation reactor 152 by way of line 154. From carbonation reactor 152 there is recovered a sodium carbonate solution, typically containing from about 2% w/v to about 5% w/v sodium carbonate, e.g. about 4% w/v sodium carbonate, which is recycled to the first stage aldolisation reactor 7 by way of lines 4 and 6.

The hydroxypivaldehyde solution in line 21 will usually contain traces of sodium compounds. Periodically some of the solid material from hydrogenation reactor 28 can be removed and washed with water to remove such sodium contamination. The resulting washings can be combined with the stream in line 16.

The overall water balance of the combined aldolisation and electrolysis plant of FIG. 1 is achieved by discharging water via line 115 such that the nett volume of the circulating aqueous phase in the whole plant remains constant.

It will be appreciated by those skilled in the art that the teachings of the invention can be applied to aldolisation of other aldehydes and the subsequent cross-Cannizzaro or hydrogenation reaction of the aldolisation intermediate products. Thus the iso-butyraldehyde feed in line 1 can be replaced by acetaldehyde, propionaldehyde, by n-butyraldehyde or an n-/iso-butyraldehyde mixture, by n-hexanal, by n-heptanal, or by n-decanal, or by a mixture of two or more of these aldehydes. If it is desired that the aldolisation intermediate be a product of the aldotrimerisation of iso-butyraldehyde then no material needs to be supplied in line 2 and the sole feed aldehyde in line 1 comprises iso-butyraldehyde.

In an alternative arrangement illustrated in FIG. 2, the decanter 146 is omitted and the liquid place leaving the anode region 127 is recycled directly to the steam stripper 105. (In FIG. 2 like parts to those in FIG. 1 are given like reference numerals). Line 106 leads directly into condenser 110. Also the gas/liquid mixture resulting from admixture of gas from line 144 with liquid from line 140 is fed in line 160 to a gas/liquid separator 161. A gas stream is vented via line 162. A liquid stream recovered in line 163 comprises water, sodium hydroxide, Kolbe reaction products and some heavy organic materials. Part of this stream is recycled to stream stripper 105 via lines 102 and 104. Another portion of the flow in line 163 is recycled via lines 122, 123 and 125 to electrolysis zone 126.

We claim:

1. A process for the production of a compound having the formula:

in which $R^1$ and $R^4$ each represent, independently of the other, a hydrogen atom, an alkyl group, an aralkyl group, or an aryl group; and $R^2$ and $R^3$ each represent, independently of the other, an alkyl group, a hydroxyalkyl group, an aralkyl group, an arylhydroxyalkyl group, or an aryl group; which process comprises:

(a) reacting one mole of a first aldehyde having at least one α-hydrogen atom and having the formula:

in which $R^5$ is a hydrogen atom, an alkyl group, an aralkyl group, or an aryl group; and $R^6$ is a hydrogen atom, an alkyl group, an aralkyl group, or an aryl group; with at least one mole of a second aldehyde having the formula:

in which $R^7$ is a hydrogen atom, an alkyl group or an aryl group; under aldolisation conditions in the presence of an aldolisation catalyst selected from alkali metal hydroxides, alkali metal carbonates, alkali metal bicarbonates, and mixtures thereof, and from alkaline earth metal hydroxides and mixtures thereof with alkali metal hydroxides, thereby to generate an intermediate aldolisation product;

(b) converting the intermediate aldolisation product of step (a) by one or more further steps including a step selected from hydrogenation and a cross-Cannizzaro reaction to the compound having the formula (I);

(c) recovering the compound having the formula (I);

(d) recovering an aqueous spent catalyst phase containing metal values and at least one Cannizzaro or cross-Cannizzaro reaction product or by-product;

(e) passing material of the spent catalyst phase to an electrolysis zone comprising an anode zone containing an anode, a cathode zone containing a cathode, and at least one ion selective barrier means separating the anode zone from the cathode zone;

(f) passing a direct current or rectified alternating current between the anode and the cathode thereby to liberate metal hydroxide in the cathode region, said metal hydroxide being selected from alkali metal hydroxides, alkaline earth metal hydroxides, and mixtures thereof;

(g) recovering liberated metal hydroxide of step (f);

(h) if necessary, converting at least a portion of the liberated metal hydroxide of step (g) to the catalyst of step (a); and (i) recycling at least one of liberated metal hydroxide of step (g) and converted metal hydroxide of step (h) for use as aldolisation catalyst in step (a).

2. A process according to claim 1, wherein step (g) comprises the steps of:

(j) recovering from the anode region of said electrolysis zone a liquid phase and gas phase;

(k) separating said liquid phase and said gas phase;

(l) steam stripping at least a portion of said liquid phase;

(m) recovering from said stream stripping step (1) an overhead fraction;

(n) condensing said overhead fraction to provide a condensed liquid phase comprising water and steam volatile organic compounds in a form substantially free of said aldolisation catalyst; and (o) recovering condensed liquid phase from said overhead fraction for recycle to the anode region of said electrolysis zone.

3. A process according to claim 1, wherein the at least one ion selective barrier means is permeable to cations from said aldolisation catalyst and wherein the spent catalyst stream from step (d) is supplied to the anode region of said electrolysis zone.

4. A process according to claim 3, wherein an aqueous phase comprising water is supplied to the cathode region of said electrolysis zone.

5. A process according to claim 1, wherein said at least one ion selective barrier means is permeable to anions and the spent catalyst stream of step (d) is supplied to the cathode region of said electrolysis zone.

6. A process according to claim 5, wherein an aqueous phase comprising water is supplied to the anode region of said electrolysis zone.

7. A process according to claim 1, wherein at least two ion selective barrier means are provided in said electrolysis zone, including a first barrier means permeable to cations and a second barrier means arranged such that said electrolysis zone comprises at least three regions, including a cathode region separated from an intermediate region by said first barrier means and an anode region separated from said intermediate region by said second barrier means, the spent catalyst stream of step (d) being supplied to said intermediate region in between said at least two barrier means.

8. A process according to claim 7, wherein an aqueous phase comprising water is supplied to one or both of the anode region and the cathode region of said electrolysis zone.

9. A process according to claim 1, wherein the anode and cathode of said one or more electrolysis cells are smooth platinum electrodes.

10. A process according to claim 1, wherein said at least one barrier means comprises a membrane permeable to ions.

11. A process according to claim 1, wherein said membrane is a supported ion exchange material.

12. A process according to claim 1, wherein the electrolysis zone is maintained at a temperature of between about 0° C. and about 100° C.

13. A process according to claim 1, wherein $R^1$, $R^4$ and $R^7$ are hydrogen atoms and $R^2$, $R^3$, $R^5$ and $R^6$ are methyl groups whereby the compound of formula (I) is neopentyl glycol, whereby the first aldehyde of formula (II) is isobutyvaldehyde, and whereby the second aldehyde of formula (III) is formaldehyde.

14. A process according to claim 13, wherein the intermediate aldolisation product is of formula:

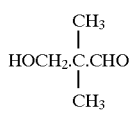

and is converted to neopentyl glycol in step (b) by a cross-Cannizzaro reaction.

15. A process according to claim 13, wherein the intermediate aldolisation product is of formula:

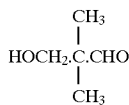

and is converted to neopentyl glycol in step (b) by hydrogenation.

16. A process according to claim 1, wherein $R^1$, $R^4$, $R^5$, $R^6$ and $R^7$ are hydrogen atoms, $R^2$ is hydroxymethyl group, and $R^3$ and $R^5$ are both ethyl groups, whereby the compound of formula (I) is 1,1,1-trimethylolpropane, whereby the first aldehyde of formula (II) is n-butyraldehyde, whereby the second aldehyde of formula (III) is formaldehyde, and wherein the conversion step (b) is a cross-Cannizzaro reaction step.

17. A process according to claim 1, wherein $R^1$, $R^4$, $R^5$, $R^6$ and $R^7$ are hydrogen atoms and $R^2$ and $R^3$ are both hydroxymethyl groups, whereby the compound of formula (I) is pentaerythritol, whereby the first aldehyde of formula (II) is acetaldehyde, and whereby the second aldehyde of formula (II) is formaldehyde.

18. A process according to claim 17, wherein the conversion step (b) is a cross-Cannizzaro reaction step.

19. A process according to claim 17, wherein the conversion step (b) is a hydrogenation step.

20. A process according to claim 1, wherein $R^1$ is isopropyl, $R^2$, $R^3$, $R^5$ and $R^6$ are methyl groups, $R^4$ is a hydrogen atom and $R^7$ is iso-proeyl, whereby the compound of formula (I) is 2,4,4-trimethylpentane-1,3-diol, and whereby the first and second aldehydes of formula (II) and (III) are each iso-butyraldehyde, wherein the intermediate aldolisation product has the formula:

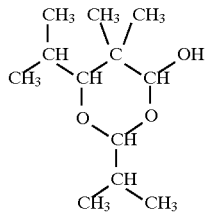

and wherein the conversion step (b) is a hydrogenation step.

21. A process for the production of polyhydroxy alcohols and glycols which comprises the steps of:

(A) subjecting at least one aldehyde to aldolisation conditions in the presence of an effective amount of an aldolisation catalyst selected from alkali metal hydroxides, alkali metal carbonates, alkali metal bicarbonates and mixtures thereof, and from alkaline earth metal hydroxides and mixtures thereof with alkali metal hydroxides to form a desired aldol intermediate;

(B) converting said aldol intermediate by means of at least one further reaction step including a reaction step selected from a hydrogenation reaction and a cross-Cannizzaro reaction to form at least one polyhydroxy alcohol or glycol;

(C) recovering from the aldol intermediate conversion step (B) a reaction mixture comprising unreacted aldehyde or aldehydes, water, aldolisation catalyst, at least one polyhydroxy alcohol or glycol, and at least one Cannizzaro or cross-Cannizzaro reaction product;

(D) separating from the reaction mixture a first aqueous phase comprising water, aldolisation catalyst and at least one Cannizzaro or cross-Cannizzaro reaction product;

(E) supplying at least a portion of said first aqueous phase to an electrolysis zone;

(F) electrolysing said portion of said first aqueous phase in said electrolysis zone to generate electrolysis products, including a metal hydroxide selected from said alkali metal hydroxide and said alkaline earth metal hydroxide;

(G) recovering from a cathode region of said electrolysis zone a second aqueous phase, the concentration of said at least one Cannizzaro or cross-Cannizzaro product in said second aqueous phase being below that in said first aqueous phase, said second aqueous phase comprising water and said metal hydroxide;

(H) if necessary converting said metal hydroxide of step (G) to the catalyst of step (A); and (I) supplying to the aldolisation step as catalyst for step (A) a material selected from the metal hydroxide of step (G) and the converted metal hydroxide of step (H).

22. A process according to claim 1, wherein aldolisation is effected in a stirred tank reactor provided with internal baffles.

23. A process according to claim 1, wherein aldolisation is carried out in an aldolisation zone with a residence time of from about 2 minutes to about 75 minutes.

24. A process according to claim 1, wherein aldolisation is carried out with an organic phase:aqueous phase ratio of from about 15:1 to about 1:15 by volume.

25. A process according to claim 1, wherein aldolisation is carried out in a tank reactor provided with a stirrer and in which the power supplied to the stirrer ranges from about 0.1 to about 3.0 kW/m³ of liquor.

* * * * *